United States Patent [19]

Okumura et al.

[11] 4,402,936
[45] Sep. 6, 1983

[54] PRESHAMPOO-TYPE HAIR-TREATING COMPOSITION

[75] Inventors: Takeo Okumura, Sakura; Hiroshi Ando, Funabashi, both of Japan

[73] Assignee: Kao Soap Co., Ltd., Tokyo, Japan

[21] Appl. No.: 235,066

[22] Filed: Feb. 17, 1981

[30] Foreign Application Priority Data

Feb. 26, 1980 [JP] Japan .................................. 55/23151

[51] Int. Cl.³ ........................ A61K 7/06; C08F 20/70
[52] U.S. Cl. .................................... 424/70; 526/295; 526/300; 526/263; 424/359
[58] Field of Search ................. 424/70, 359; 526/295, 526/300, 303.1, 263

[56] References Cited

U.S. PATENT DOCUMENTS

| 3,912,808 | 10/1975 | Sokol | 424/70 |
| 3,927,199 | 12/1975 | Micchelli et al. | 424/359 |
| 3,988,438 | 10/1976 | Weinstein | 424/359 |
| 4,175,572 | 11/1979 | Hsiung et al. | 424/70 |
| 4,287,172 | 9/1981 | Jacquet et al. | 424/70 |

Primary Examiner—Delbert R. Phillips
Assistant Examiner—F. T. Moezie
Attorney, Agent, or Firm—Flynn, Thiel, Boutell & Tanis

[57] ABSTRACT

A preshampoo-type, hair-treating composition comprising a polymer having a cyclic cationic group, and optionally containing a peptide having a molecular weight of 300 to 10,000.

7 Claims, No Drawings

PRESHAMPOO-TYPE HAIR-TREATING COMPOSITION

The present invention relates to a preshampoo-type, hair-treating composition. More particularly, the present invention relates to a preshampoo-type, hair-treating composition comprising a polymer containing a cyclic cationic group, optionally together with a specific peptide.

Hair is very readily contaminated with external contaminants and products formed by decomposition and oxidation of sebaceous substances secreted from the head skin. Anionic surface active agents, amphoteric surface active agents and other surface active agents have been used as main components of shampoo compositions for washing away dirt and contaminants adhering to hair. However, these surface active agents wash away not only the dirt and contaminants, but also sebaceous substances which impart a desirable flexible and soft touch and feel to hair. Hair from which these sebaceous substances have been removed has a bad touch and feel. Combing or brushing of such hair is very difficult and hair breakage and split ends are readily caused because such hair is damaged by combing or brushing. For preventing the occurrence of such troubles at the time of hair-washing and improving the finishing effect on the washed hair, additives, such as oils and fats or a polymeric compound, are incorporated in shampoo compositions. Recently, a preshampoo-type, hair-treating agent comprising an oil or fat, such as hydrous lanolin, has been marketed as an important product for protecting hair, and this hair-treating agent has gained public favor. This preshampoo-type, hair-treating agent is applied to the hair and then hair-washing is carried out by the conventional procedure. Damage to the hair during hair-washing and finishing treatments, such as rinsing and drying with a drier, is prevented and a conditioning effect is imparted to the washed hair to give it a more natural appearance and feel and to provide lustre and bounce. However, hair treated with such a treating agent comprising an oil or fat, such as hydrous lanolin, as a main effective ingredient, have a relatively heavy and thick feel and the hair becomes sticky in some cases. Accordingly, a further improvement has been desired in hair-treating agents of the preshampoo-type.

We have conducted investigations with a view to developing a hair-treating agent satisfying this requirement and, surprisingly, we have discovered that a preshampoo-type, hair-treating composition comprising a specific cationic polymer, as the main effective ingredient, overcomes the foregoing defect, Moreover, if a peptide of a specific molecular weight, which is a decomposition product of an oil or fat, or a skin protein, is further incorporated in the composition, the effect is further enhanced. We have now completed the present invention based on this discovery.

The specific cationic polymer that is used in the present invention is a polymeric derivative of a monomer containing a cyclic cationic group. Homopolymers or copolymers of a diallyl quaternary ammonium compound or a vinylpyridine cationic polymer are preferred. Specific examples of such preferred polymers are described below.

(i) Homopolymers of diallyl quaternary ammonium compounds represented by the following formulae:

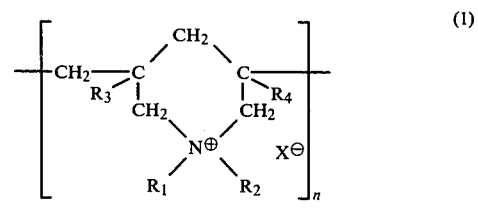

and

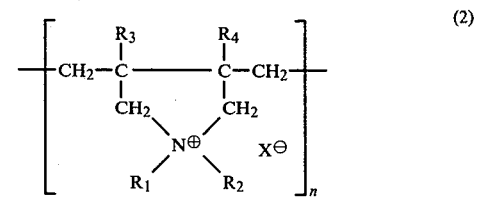

wherein $R_1$ and $R_2$, which may be the same or different, stand for a hydrogen atom or an alkyl group having 1 to 18 carbon atoms, preferably 1 to 4 carbon atoms, $R_3$ and $R_4$, which may be the same or different, stand for a hydrogen atom, an alkyl group having 1 to 3 carbon atoms or a phenyl group, $X^-$ stands for an anionic residue, a halogen ion such as chlorine or bromine, an inorganic acid residue such as sulfuric acid or nitric acid or an organic acid residue such as methyl sulfate or hydroxycarboxylic acid, and n is a number providing a molecular weight of 10,000 to 1,000,000.

(ii) Copolymers of diallyl quaternary ammonium compounds represented by the following formulae:

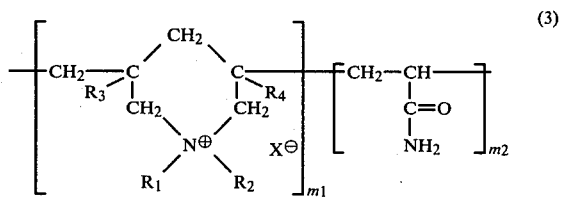

and

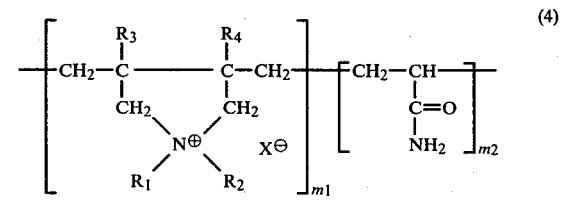

wherein $R_1$, $R_2$, $R_3$, $R_4$ and $X^\ominus$ have the same meanings as defined above in the formulae (1) and (2), and $m_1$ and $m_2$ are numbers providing a molecular weight of 10,000 to 1,000,000 for the polymer.

(iii) Vinylpyridine cationic polymers repesented by the following formula:

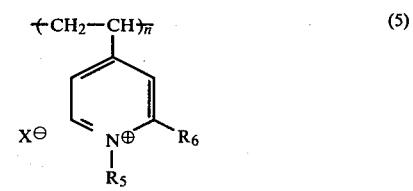

wherein $R_5$ and $R_6$, which may be the same or different, stand for a hydrogen atom, an alkyl group having 1 to 6 carbon atoms or a phenyl group, and n and $X^\ominus$ have the same meanings as defined above in the formulae (1) and (2).

It is preferred that such polymer containing a cyclic cationic group is incorporated in an amount of 0.1 to 5% by weight (hereinafter referred to as "%") into the preshampoo-type, hair-treating composition.

We found that when a product obtained by decomposition of a hair or skin protein is used in combination with the above-mentioned polymer containing a cyclic cationic group, the effect of the preshampoo-type, treating composition is further improved. Based on this finding, we have completed the second aspect of the present invention.

In the second aspect of the present invention, it is critical that a peptide having a molecular weight of 300 to 10,000 should be incorporated and used in combination with the above-mentioned polymer containing a cyclic cationic group. Such peptide having a molecular weight of 300 to 10,000 is prepared by enzymatically decomposing a skin protein, collagen or gelatin, and hydrolyzing the resulting low-molecular-weight product with an acid or alkali. In the present invention, it is critical that the molecular weight of the peptide used should be 300 to 10,000, but it is preferred that the molecular weight of the peptide be 500 to 3,000, especially 600 to 1,600. Such peptide can easily be obtained by hydrolyzing a commercially available, enzymatically decomposed peptide with an acid or alkali. According to the invention, it is preferred that the peptide is of the type obtained by hydrolyzing collagen. Peptides which are available in the market are LEXEIN X-250 (m.w.: 500–10,000) of Inolex, BYCO A (m.w.: 1000–2000) of Croda, Promois W-32 (m.w.: 400) of Seiwa Kasei, Promois W-52 (m.w.: 2000) of Seiwa Kasei, Nutrilan J, (m.w.: 1100–1300) of Chem. Fabrik Grünan, NP-600 (m.w.: 600) of Nippi Inc. and NP-100 (m.w.: 1000) of Nippi Inc.

It is preferred that the peptide be incorporated in an amount of 0.1 to 5 wt. % in the preshampoo-type, hair-treating composition, and it also is preferred that the weight ratio of the polymer containing a cyclic cationic group to the peptide be in the range of from 10/1 to 1/50.

The excellent effects attained in the present invention cannot be attained at all when the specific polymer containing a cyclic cationic group, that is used in the present invention, is incorporated in a shampoo composition comprising an anionic surface active agent or an amphoteric surface active agent.

In addition to the above-mentioned critical components, the balance of the composition of the present invention can be water. The composition, according to the invention, can further comprise optional components, for example, an oil or fat, such as a higher alcohol or fatty acid ester, a nonionic surface active agent acting as an emulsifier and solubilizing agent, such as polyoxyalkylene alkyl ether, a moisture-retaining agent such as glycerin, pyrrolidone-carboxylic acid or propylene glycol, a perfume and a dye.

The present invention will now be described in detail with reference to the following illustrative Examples that by no means limit the scope of the invention.

The effects to the preshampoo-type, hair-treating compositions were evaluated according to the following methods.

(1) FEEL OF HAIR DURING HAIR-WASHING

A bundle of hair of a Japanese woman having a length of 20 cm and a weight of 20 g was coated with 2 g of a preshampoo-type, hair-treating composition, the hair bundle was allowed to stand still for 5 minutes and then it was washed for 1 minute with 2 g of a commercially available plain shampoo according to a conventional procedure. At this point, the feel of the hair was organoleptically tested. More specifically, a hair bundle treated with a commercially available preshampoo-type, hair-treating composition comprising hydrous lanolin, as the main effective ingredient, was used as a reference hair bundle, and a pair-comparison organoleptic test was conducted by a panel of 20 experts. The feel of the hair bundle was evaluated according to the following scale (an average of the values assigned by the 20 experts is set forth in the following tables).

| Point | Evaluation |
| --- | --- |
| +2 | feel is significantly better than that of the reference hair bundle |
| +1 | feel is slightly better than that of the reference hair bundle |
| 0 | feel is equivalent to that of the reference hair bundle |
| −1 | feel is slightly inferior to that of the reference hair bundle |
| −2 | feel is significantly inferior to that of the reference hair bundle |

(2) FEEL OF HAIR IN WET STATE AND COMBING PROPERTY

After completion of the evaluation of the feel during hair-washing, the hair bundle was rinsed for 1 minute with running water at 40° C., and then the water was removed by wiping the hair bundle with a towel. The feel of the hair bundle in the wet state was evaluated in the same manner as described above. Then, the hair bundle was combed by using a commercially available nylon comb and the ease of the combing operation was evaluated. The evaluation standard was the same as described in (1) above.

(3) MEASUREMENT OF FORCE NECESSARY FOR COMBING HAIR IN WET STATE

After evaluation of the hair feel and ease of the combing operation in the wet state, the hair bundle was fixed to a strain gauge and a nylon comb was passed through the hair bundle 20 times in succession. In each combing, the resistance value was measured, and the average value was calculated as the combing force.

(4) FEEL, COMBING PROPERTY, ARRANGEMENT EASE AND COMBING FORCE AFTER DRYING

After the measurement of the combing force in the wet state, the hair bundle was air-dried, and the foregoing properties were evaluated according to the methods described in (1), (2) and (3) above.

EXAMPLE 1

Effects of the polymer containing a cyclic cationic group and the peptide were examined. The results shown in Table 1 were obtained.

TABLE 1

|  | Sample 1 | Sample 2 | Sample 3 | Sample* 4 |
|---|---|---|---|---|
| Composition (wt. %) | | | | |
| poly(dimethyldiallyl ammonium chloride) having molecular weight of 100,000 | 1 | 1 | | 1 |
| peptide having molecular weight of 1,500 | | 3 | 3 | 3 |
| polyoxyethylene(10) cetyl ether | 2 | 2 | 2 | 2 |
| triethanolamine lauryl sulfate | | | | 15 |
| lauric diethanolamide | | | | 3 |
| perfume | appropriate amount | appropriate amount | appropriate amount | appropriate amount |
| water | balance | balance | balance | balance |
| Effects on Hair | | | | |
| feel of hair during hair-washing | +0.9 | +1.1 | −0.1 | −0.3 |
| washed hair in wet state | | | | |
| feel of hair | +1.0 | +1.0 | −0.5 | −0.4 |
| ease of combing operation | +1.0 | +1.3 | −0.5 | −0.2 |
| combing force (g) | 300 | 210 | 500 | 450 |
| hair after drying | | | | |
| feel of hair | +1.1 | +1.5 | −0.1 | −0.8 |
| ease of combing operation | +0.9 | +1.3 | −0.3 | 0.0 |
| combing force (g) | 180 | 130 | 310 | 280 |
| manageability | +1.1 | +1.4 | −0.4 | 0.0 |

Note
*this sample was used as a shampoo composition and the hair was washed according to a conventional procedure.

EXAMPLE 2

The effects of various cationic polymers were examined. The results shown in Table 2 were obtained.

TABLE 2

|  | Sample 5 | Sample 6 | Sample 7 | Sample 8 | Sample 9 | Sample 10 |
|---|---|---|---|---|---|---|
| Composition (wt. %) | | | | | | |
| peptide having molecular weight of 1,000 | 3 | 3 | 3 | 3 | 3 | 3 |
| vinylpyridine cationic polymer[1] having molecular weight of 20,000 | 1 | | | | | |
| diallyl quaternary ammonium[2] copolymer having molecular weight of 100,000 | | 1 | | | | |
| cationic cellulose (Polymer JR-400 supplied by UCC) | | | 1 | | | |
| cationic starch | | | | 1 | | |
| cationic polymer[3] (GAF COAT 734 supplied by GAF Corp.) | | | | | 1 | |
| cationic polymer[4] (Cartlex L supplied by National Starch Co.) | | | | | | 1 |
| water | 96 | 96 | 96 | 96 | 96 | 96 |
| Effects on Hair | | | | | | |
| feel of hair during hair-washing | +1.3 | +1.2 | +0.2 | −0.3 | −0.3 | −0.3 |
| combing property in wet state after hair-washing | +1.0 | +1.1 | +0.2 | +0.1 | −0.3 | −0.4 |

Note
[1] $R_6 = CH_3$, $R_5 = H$
[2] $R_1 = R_2 = CH_3$, $R_3 = R_4 = H$
[3] cationic vinylpyrrolidone/dimethylaminoethyl methacrylate copolymer
[4] aminoethyl acrylate/methacrylic acid/methacrylate copolymer

EXAMPLE 3

The effects of the molecular weight of the peptide were examined. The results shown in Table 3 were obtained.

| Composition: | |
|---|---|
| Poly(dimethyldiallyl ammonium chloride) having a molecular weight of 100,000 | 2% |
| Peptide having a molecular weight shown in Table 3 | 2% |
| Water | 96% |

TABLE 3

| Molecular Weight | Arrangement Ease After Drying |
|---|---|
| 200 | 0.0 |
| 600 | +1.4 |
| 1600 | +1.4 |
| 10000 | +0.9 |
| 20000 | +0.3 |

EXAMPLE 4

The properties of the composition of the present invention described below were evaluated with those of a commercially available preshampoo-type, hair-treating composition by a panel of 50 women. Result are shown in Table 4.

| Composition (wt. %) | Ratio (%) |
|---|---|
| poly(dimethyldiallyl (Merquat 100) ammonium chloride) | 1.0 |
| peptide having molecular (NP-1000) weight of 1,000 | 3.0 |
| polyoxyethylene(20) oil ether | 2.0 |
| propylene glycol | 2.0 |
| hydroxyethyl cellulose | 0.3 |
| methylparaben | 0.2 |
| perfume | 0.1 |

-continued

| Composition (wt. %) | Ratio (%) |
| --- | --- |
| pigment | appropriate amount |
| water | balance |
| | 100.00 |

Note

A bundle of hair of a Japanese woman having a length of 20 cm and a weight of 20 g was coated with 15 g of preshampoo-type, hair-treating composition, the hair bundle was allowed to stand still for 3 minutes and then it was washed lightly and washed with 15 g of a commercially available plain shampoo according to a conventional procedure.

TABLE 4

| Evaluation Items | Number of those who answer the present invention is better | Number of those who answer no difference | Number of those who answer commercially available is better |
| --- | --- | --- | --- |
| total evaluation | 38 persons | 7 persons | 5 persons |
| feel of hair during hair-washing washed hair in wet state | 31 | 10 | 9 |
| feel of hair | 34 | 9 | 7 |
| ease of combing operation hair after drying | 33 | 8 | 9 |
| feel of hair | 38 | 7 | 5 |
| ease of combing operation | 41 | 5 | 4 |
| manageability | 40 | 7 | 3 |

The embodiments of the invention in which an exclusive property or privilege is claimed are defined as follows:

1. A preshampoo-type, hair-treating composition consisting essentially of from 0.1 to 5% by weight of a polymer selected from the group consisting of
   1. polymers having the formulas

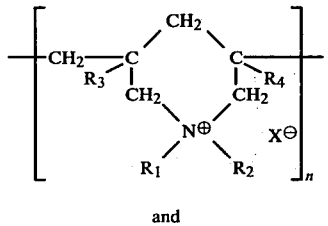

and

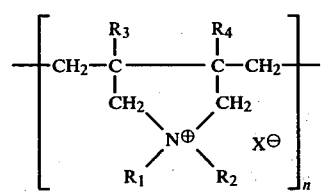

wherein $R_1$ and $R_2$, which are the same or different, are hydrogen or alkyl having 1 to 18 carbon atoms; $R_3$ and $R_4$, which are the same or different, are hydrogen, alkyl having 1 to 3 carbon atoms or phenyl, $X^\ominus$ is an anionic group, and n is a number such that the molecular weight of the polymer is from 10,000 to 1,000,000, 2. copolymers having the formulas

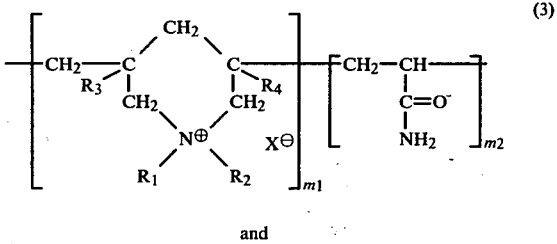

and

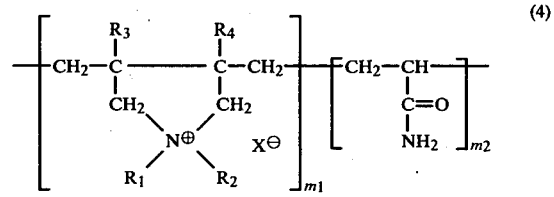

wherein $R_1$, $R_2$, $R_3$, $R_4$ and $X^\ominus$ have the same meanings as defined above and $m_1$ and $m_2$ are numbers such that the molecular weight of the polymer is from 10,000 to 1,000,000, 3. polymers having the formula

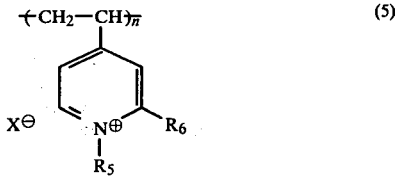

wherein $R_5$ and $R_6$, which are the same or different, are hydrogen, alkyl having 1 to 6 carbon atoms or phenyl, and n and $X^\ominus$ have the same meanings as defined above, from 0.1 to 5% by weight of a peptide prepared by enzymatically decomposing hair protein, skin protein, collagen or gelatin, and then hydrolyzing the resulting relatively low-molecular-weight product, said peptide having a molecular weight of from 300 to 10,000, and the balance is essentially water, said composition being free of anionic and amphoteric surface active agents.

2. A preshampoo-type, hair-treating composition as claimed in claim 1, wherein the mixing weight ratio of said polymer to said peptide is in the range of from 10/1 to 1/50.

3. A preshampoo-type hair-treating composition as claimed in claim 1, wherein the molecular weight of the peptide is in the range of from 600 to 1,600.

4. A method of treating human hair which comprises applying to dry human hair a preshampoo-type hair-treating composition as claimed in claim 1, so as to coat the hair substantially uniformly with said composition, and then shampooing and drying said hair.

5. A preshampoo-type, hair-treating composition consisting essentially of from 0.1 to 5% by weight of a polymer having the formula

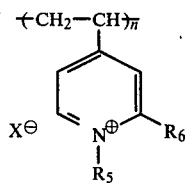

wherein $R_5$ and $R_6$, which are the same or different, are hydrogen, alkyl having 1 to 6 carbon atoms or phenyl, n is a number such that the molecular weight of the polymer is from 10,000 to 1,000,000, and $X^{\ominus}$ is an anionic group, and the balance is essentially water, said composition being free of anionic and amphoteric surface active agents.

6. A preshampoo-type, hair-treating composition consisting essentially of from 0.1 to 5% by weight of a polymer having the formula

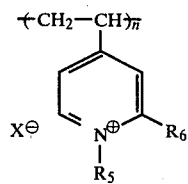

wherein $R_5$ and $R_6$, which are the same or different, are hydrogen, alkyl having 1 to 6 carbon atoms or phenyl, n is a number such that the molecular weight of the polymer is from 10,000 to 1,000,000, and $X^{\ominus}$ is an anionic group, from 0.1 to 5% by weight of a peptide prepared by enzymatically decomposing hair protein, skin protein, collagen or gelatin, and then hydrolyzing the resulting relatively low-molecular-weight product, said peptide having a molecular weight of from 300 to 10,000, and the balance is essentially water, said composition being free of anionic and amphoteric surface active agents.

7. A method of treating human hair which comprises applying to dry human hair a preshampoo-type, hair-treating composition as claimed in claim 5, so as to coat the hair substantially uniformly with said composition, and then shampooing and drying said hair.

* * * * *